(12) United States Patent
Hanebuchi et al.

(10) Patent No.: US 9,709,383 B2
(45) Date of Patent: Jul. 18, 2017

(54) OPTICAL COHERENCE TOMOGRAPHY APPARATUS

(71) Applicant: NIDEK CO., LTD., Gamagori, Aichi (JP)

(72) Inventors: Masaaki Hanebuchi, Nukata (JP); Keiji Murata, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 0 days.

(21) Appl. No.: 15/141,142

(22) Filed: Apr. 28, 2016

(65) Prior Publication Data

US 2016/0320171 A1 Nov. 3, 2016

(30) Foreign Application Priority Data

Apr. 30, 2015 (JP) ................................. 2015-093725

(51) Int. Cl.
*G01B 9/02* (2006.01)
*A61B 3/12* (2006.01)
(Continued)

(52) U.S. Cl.
CPC .......... *G01B 9/02091* (2013.01); *A61B 3/102* (2013.01); *A61B 3/1233* (2013.01);
(Continued)

(58) Field of Classification Search
CPC ............ G01B 9/02027; G01B 9/02087; G01B 9/02091
See application file for complete search history.

(56) References Cited

U.S. PATENT DOCUMENTS

2011/0234786 A1* 9/2011 Yuasa .................... A61B 3/102
348/78
2012/0053904 A1 3/2012 Yuasa et al.
(Continued)

FOREIGN PATENT DOCUMENTS

JP 2010-259698 A 11/2010
JP 2013-007601 A 1/2013
(Continued)

OTHER PUBLICATIONS

Sep. 21, 2016 Search Report issued in European Patent Application No. 16167635.8.

*Primary Examiner* — Jonathan Hansen
(74) *Attorney, Agent, or Firm* — Oliff PLC

(57) ABSTRACT

An optical coherence tomography apparatus includes: an OCT light source; a first light splitter configured to split an optical path into a first measurement optical path and a reference optical path; a light guide optical system including a second light splitter, configured to guide the measurement light to a test substance through the second light splitter, the second light splitter splitting the reflected light into the first and second measurement optical paths; a detection optical system detecting first interference between the reflected light having passed through the first measurement optical path and the reference light, and second interference between the reflected light having passed through the second measurement optical path and the reference light; and a calculation controller processing an output signal which is output from the detection optical system to obtain OCT data regarding the test substance.

13 Claims, 3 Drawing Sheets

(51) Int. Cl.
    *A61B 3/10*  (2006.01)
    *A61B 5/00*  (2006.01)
    *G01N 21/47* (2006.01)
    *G01N 21/21* (2006.01)

(52) U.S. Cl.
    CPC ........ *A61B 5/0066* (2013.01); *G01B 9/02019* (2013.01); *G01B 9/02028* (2013.01); *G01B 9/02087* (2013.01); *G01B 2290/45* (2013.01); *G01B 2290/70* (2013.01); *G01N 21/21* (2013.01); *G01N 21/4795* (2013.01)

(56) References Cited

U.S. PATENT DOCUMENTS

| | | | |
|---|---|---|---|
| 2012/0120408 A1 | 5/2012 | Yasuno et al. | |
| 2012/0327423 A1 | 12/2012 | Hanebuchi | |
| 2013/0155414 A1* | 6/2013 | Hatada | G01B 9/02007 356/489 |
| 2013/0185023 A1* | 7/2013 | Vakoc | A61B 3/102 702/189 |
| 2016/0106319 A1 | 4/2016 | Yasuno et al. | |
| 2016/0313112 A1* | 10/2016 | Yamanari | A61B 3/102 |

FOREIGN PATENT DOCUMENTS

| | | |
|---|---|---|
| JP | 2013-148482 A | 8/2013 |
| JP | 2014-228473 A | 12/2014 |
| WO | 2010/143601 A1 | 12/2010 |

* cited by examiner

OPTICAL COHERENCE TOMOGRAPHY APPARATUS

CROSS REFERENCE TO RELATED APPLICATION

This application is based upon and claims the benefit of priority of Japanese Patent Application No. 2015-093725 filed on Apr. 30, 2015, the contents of which are incorporated herein by reference in its entirety.

BACKGROUND

The present disclosure relates to an optical coherence tomography apparatus measuring a test substance by using light interference between measurement light and reference light.

As an optical coherence tomography apparatus measuring a test substance by using light interference between measurement light and reference light, there is a two-beam type optical coherence tomography apparatus in which measurement light is split into a plurality of beams (refer to WO2010/143601 and JP-A-2010-259698).

As a configuration for measuring polarization characteristics of a test substance, there is a polarization sensitive OCT (PS-OCT).

Apparatuses obtained by improving the above-described apparatus are disclosed in Patent Documents 3 and 4, and obtain a plurality of tomographic images with a single light detector by using an optical delay path.

SUMMARY

The techniques disclosed in WO2010/143601 and JP-A-2010-259698 are complex in that two spectrometers are necessary, and polarized light is required to be split into two light beams, and thus have room for improvement in terms of practical use.

In a case of the polarization sensitive OCT, in order to acquire a plurality of tomographic images regarding the same part, a plurality of tomographic images are required to be extracted from tomographic images which are continuously acquired at a predetermined frame rate, or it is necessary to provide a plurality of detection systems.

The apparatuses disclosed in JP-A-2013-7601 and JP-A-2013-148482 also have room for improvement in that light returning from the eye is attenuated by a splitter or the like.

An object of the present disclosure is to provide an optical coherence tomography apparatus capable of improving at least one aspect of the related art.

In order to solve the problems, the present disclosure is characterized in terms of including the following configurations.

An optical coherence tomography apparatus includes:
an OCT light source configured to emit a light;
a first light splitter configured to split an optical path of light emitted from the OCT light source into a first measurement optical path by which measurement light is guided and a reference optical path by which a reference light is guided;
a light guide optical system including a second light splitter through which the measurement light from the first measurement optical path is guided, the light guide optical system being configured to guide the measurement light to a test substance through the second light splitter, the second light splitter being configured to split light reflected from the test substance based on the measurement light, into the first measurement optical path and a second measurement optical path;
a detection optical system configured to detect first interference between the reflected light having passed through the first measurement optical path and the reference light, and second interference between the reflected light having passed through the second measurement optical path and the reference light; and
a calculation controller configured to process an output signal which is output from the detection optical system to obtain OCT data regarding the test substance.

DESCRIPTION OF ILLUSTRATIVE EMBODIMENTS

Figure 1:
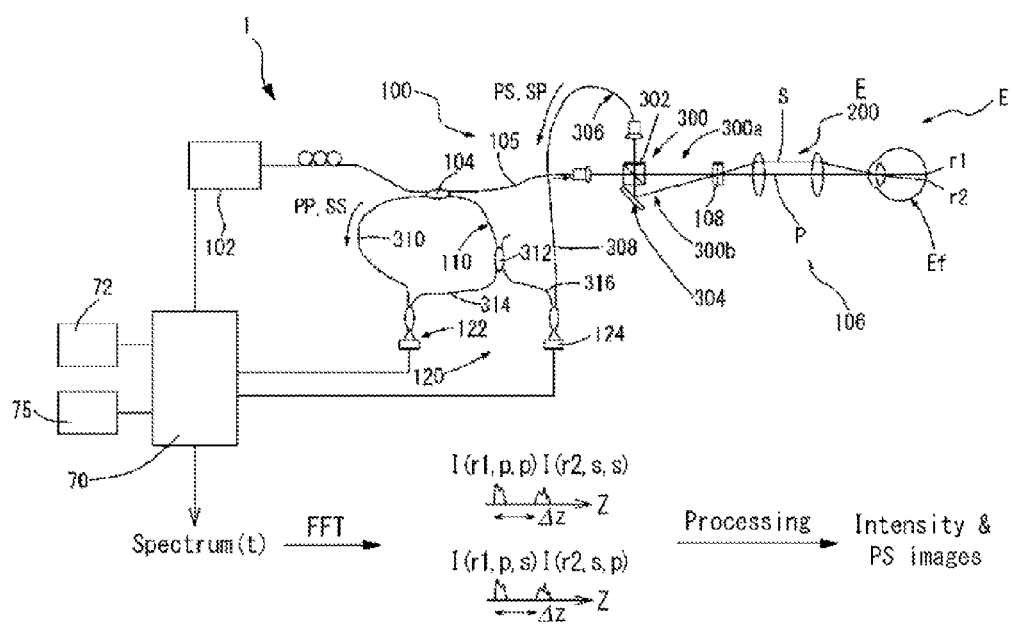
FIG. 1 is a diagram for explaining an apparatus configuration according to the present embodiment.

An apparatus according to the present disclosure will be described with reference to the drawings.

An optical coherence tomography apparatus according to the present embodiment may include a light guide optical system (for example, a light guide optical system 200) provided with a first light splitter (for example, a coupler 104) and a second light splitter (for example, a polarized beam splitter 302); a detection optical system (for example, a detector 120), and a calculation controller (for example, a calculation controller 70). The first light splitter and the second light splitter may be optical path splitters that split an optical path, and may employ an optical member for splitting an optical path.

The first light splitter may split an optical path of light emitted from an OCT light source (for example, a light source 102) into a first measurement optical path (for example, an optical fiber 105) and a reference optical path (for example, a reference optical system 110). The light guide optical system may guide measurement light (also referred to as sample light) from the first measurement optical path to a test substance via the second light splitter. The light guide optical system may include, for example, an objective lens system, and may include, for example, an objective mirror system.

The second light splitter may split an optical path of reflected light from the test substance, based on measurement light, into the first measurement optical path and a second measurement optical path (for example, an optical fiber 306). The second light splitter may be disposed on the measurement optical path. The second light splitter may return reflected light from the test substance, based on the measurement light, to the first measurement optical path, and also newly guides the reflected light to the second measurement optical path. The second light splitter may split an optical path of reflected light from the test substance into three or more optical paths.

The second light splitter may split measurement light from the first measurement optical path into first measurement light (for example, first measurement light (P)) and second measurement light (for example, second measurement light (S)). The second light splitter may have a characteristic of transmitting the first measurement light therethrough and of reflecting the second measurement light. The second light splitter may have a characteristic of splitting measurement light from the first measurement optical path into the first measurement light and the second measurement light whose polarization components are different from each other. In this case, the measurement light may be split into three or more measurement light beams.

The detection optical system may detect first interference which is interference between reflected light having passed through the first measurement optical path and reference light having passed through the reference optical path, and second interference which is interference between the reflected light having passed through the second measurement optical path and reference light having passed through the reference optical path. The detection optical system may include a light detector (for example, a detector 120). The detection optical system may separately include a first light detector which detects the first interference and a second light detector which detects the second interference. The detection optical system may detect the first interference and the second interference by using a single detector.

The calculation controller may process an output signal which is output from the detection optical system so as to obtain OCT data of the test substance. The acquired OCT data may not only be a shape tomographic image but also functional OCT data such as motion contrast data or polarization characteristic data.

<Basic Configuration>

An OCT apparatus (for example, an OCT apparatus 1) may have a Fourier domain optical coherence tomography (FD-OCT) as a basic configuration. The OCT apparatus includes, for example, an OCT optical system (for example, an OCT optical system 100) and a calculation controller (for example, a controller 70). The technique regarding the present apparatus is applied to, for example, a polarization sensitive OCT (PS-OCT), but may also be applied to a standard OCT for detecting reflection intensity from a test substance, and OCT angiography (for example, a Doppler OCT) for detecting motion contrast data of a test substance. A multifunction OCT in which the PS-OCT and the OCT angiography are combined with each other may be employed. Representatives of the FD-OCT are a swept source-OCT (SS-OCT) and a spectral domain OCT (SD-OCT).

The OCT optical system may have a configuration related to an interference system for obtaining a tomographic image (OCT tomographic image) of a test substance by using an OCT principle. The OCT optical system may include a splitter (light splitter), a measurement optical path, a reference optical path, a combiner (light combiner), and a light detector (hereinafter, referred to as a detector). The splitter (for example, a coupler 104) may split an optical path of light from a light source (for example, a light source 102) into the measurement optical path and the reference optical path. As the splitter and the combiner, for example, a beam splitter, a half mirror, a fiber coupler, and a circulator are used. The measurement optical path may have a configuration for guiding light to a test substance. The reference optical path may have a configuration for causing light to travel inside the apparatus so that the light interferes with measurement light. The combiner may combine (interfere) measurement light from the measurement optical path, reflected at a test substance, with reference light from the reference optical path. The detector (for example, a detector 120) may receive interference signal light which is caused by interference between measurement light and reference light. An optical scanner (for example, an optical scanner 108) may be provided on the measurement optical path, and the optical scanner is used to scan a test substance with measurement light.

The calculation controller (hereinafter, referred to as a controller) may perform a control process, an image process, a calculation process, and the like on each constituent element of the apparatus. For example, the controller may obtain OCT data by processing a detection signal from the detector. The controller may obtain spectral signals including interference signal light at each wavelength so as to process the spectral signals. The controller may process the spectral signals so as to obtain data (depth information) regarding a test substance in a depth direction.

The controller may arrange depth information obtained at different positions through scanning with measurement light so as to obtain information (shape information, polarization characteristics, and the like) regarding a test substance. The controller may store the obtained results in a storage unit (for example, a memory 72). The controller may display the obtained results on a display unit (for example, a monitor 75) (image display unit).

The spectral signal (spectral data) may be rewritten as a function of a wavelength $\lambda$ so as to be converted into a function $I(k)$ with the same interval with respect to a wave number k ($=2\pi/\lambda$). Alternatively, the spectral signal may be acquired as the function $I(k)$ with the same interval with respect to the wave number k from the beginning (K-CLOCK technique). The controller may perform Fourier transform on the spectral signal in a wave number k space so as to obtain OCT data in a depth (Z) region.

Information obtained as a result of the Fourier transform may be expressed as a signal including a real number component and an imaginary number component in the Z space. The controller may obtain absolute values of the real number component and the imaginary number component of the signal in the Z space so as to acquire an A scan signal (a signal intensity value in the depth direction). The controller may arrange A scan signals obtained at different positions so as to obtain a tomographic image of a test substance.

The test substance may not only be the eye (an anterior chamber, a fundus, and the like), and the skin, but also materials other than a living body.

<Spectral Multiplexing Technique>

The OCT optical system according to the present embodiment may be provided with an optical path length difference generator (for example, an optical delay path 300) which generates at least two light beams having optical path length differences from each other. The optical path length difference generator may be an optical delay path. The optical path length difference generator may include a standard optical path and a bypass optical path. The optical path length difference generator may be disposed on at least one of the measurement optical path and the reference optical path.

The optical path length difference generator may include, for example, a second light splitter (for example, a polarized beam splitter 302). The light splitter may split an optical path into a standard optical path (a standard route 300a) and a bypass optical path (for example, a bypass route 300b). An optical path length difference provided by the optical delay path may be set so that a tomographic image formed by one light beam is formed on the front side, and a tomographic image formed by the other light beam is formed on the rear side, in an imaging range of tomographic images in the depth direction. A light splitter used in the optical delay path may be a half mirror, a beam splitter (for example, a polarized beam splitter), a fiber coupler, or a circulator. The light splitter may include an optical path splitter which splits an optical path into at least two paths. The optical delay path may generate an optical path length difference between two measurement light beams obtained as a result of splitting in the light splitter.

The optical path length difference generated by the optical path length difference generator causes a plurality of interference signal light beams having optical path length differences from each other. The interference signal light caused by interference between measurement light and reference light includes first interference signal light based on the standard optical path and second interference signal light based on the bypass optical path. A polarized light splitter (for example, a polarized beam splitter 302) is provided on the optical delay path, and thus it is possible to obtain a plurality of interference signal light beams corresponding to different polarization states.

Interference signal light at each wavelength may be received by the detector so as to be detected by the detector as a spectral signal. The light detector may detect a first spectral signal and a second spectral signal having optical path length differences from each other. In this case, the first spectral signal and the second spectral signal are multiplexed into the spectral signal. The first spectral signal includes first interference signal light at each wavelength, and the second spectral signal includes second interference signal light at each wavelength. The first spectral signal and the second spectral signal differ in the density of interference fringes formed by spectra due to the optical path length difference. A polarized light splitter (for example, a polarized beam splitter) may be provided on the optical delay path so that a plurality of spectral signals differing in mutual polarization states are detected. In this case, a plurality of spectral signals differing in mutual process states are multiplexed into the spectral signal.

The controller may process the multiplex spectral signal from the detector so as to obtain OCT data regarding a test substance in the depth direction. Depth information includes depth information (for example, first depth information I(r1,p,p) and second depth information I(r1,p,s)) corresponding to the first spectral signal, and depth information (for example, third depth information I(r2,s,s) and fourth depth information I(r2,s,p)) corresponding to the second spectral signal. The depth information corresponding to the first spectral signal and the depth information corresponding to the second spectral signal are acquired in a state of being separated in the depth direction. Such depth information may be obtained, for example, in the same region on a test substance.

The controller processes, for example, multiplex spectral signals at respective positions in a crossing direction so as to obtain tomographic image data including a plurality of tomographic images of the test substance together. The tomographic image data includes tomographic images (for example, a first tomographic image TPP and a second tomographic image TPS) corresponding to the first spectral signal, and tomographic images (for example, a third tomographic image TSS and a fourth tomographic image TSP) corresponding to the second spectral signal.

First, it is advantageous to use the depth information based on the multiplex spectral signal, for example, for detection of a polarization state of a test substance in a PS-OCT.

Second, the depth information based on the multiplex spectral signal includes a plurality of tomographic images of a test substance, and thus it is advantageous to use the depth information, for example, for image combining processes (for example, an addition averaging process and a motion contrast measurement process). Consequently, it is possible to acquire a combined image within a short period of time.

For example, the controller 70 may perform positioning between a plurality of tomographic images which are formed at different positions in the depth direction so as to obtain an addition average image (or a motion contrast image).

As a wavelength variable light source used in an SS-OCT, it is advantageous to use a wavelength variable light source with a narrow instantaneous emission line width. By using such a light source, two tomographic images having different optical path lengths are maintained to have substantially the same interference intensity, and are also acquired in a state of being separated from each other. Regarding an imaging range, a range including a plurality of tomographic images which are separated from each other in the depth direction is secured.

<Application to PS-OCT>

In a case where the apparatus of the present embodiment is applied to the PS-OCT, a polarized light generator (for example, the polarized beam splitter 302) for generating a plurality of light beams having different polarization components may be provided on the measurement optical path (for example, the optical delay path 300). The polarized light generator may generate a plurality of light beams in which polarization components are orthogonal to each other, and, for example, may have a configuration of generating linearly polarized light beams which are orthogonal to each other, or a configuration of generating circularly polarized light beams which are orthogonal to each other. In a case where the circularly polarized light is generated, for example, a ¼ wavelength plate may be disposed between the polarized beam splitter and a subject's eye so that the circularly polarized light is formed. Polarization components of a plurality of generated light beams may not necessarily be orthogonal to each other. The polarized light generator may generate linearly polarized light and circularly polarized light. A test substance is irradiated with first measurement light (P) and second measurement light (S) having different polarization components by the polarized light generator.

In this case, a detection optical system may detect interference between polarized reflected light which is reflected light based on the plurality of measurement light beams (for example, the first measurement light (P) and the second measurement light (S)) generated by the polarized light generator, and reference light. The detection optical system may detect first interference which is interference between polarized reflected light having traveled through the first measurement optical path and the reference light having traveled through the reference optical path, and second interference which is interference between polarized reflected light having traveled along the second measurement optical path and the reference light having traveled along the reference optical path.

Here, the light splitter based on the detection optical system may detect interference between polarized reflected light from a test substance, based on the first measurement light and the reference light, and interference between polarized reflected light from a test substance, based on the second measurement light and the reference light. Here, the first measurement light reflected from the test substance may include first polarized reflected light (PP) whose polarization direction is maintained at the reflection, and second polarized reflected light (PS) whose polarization direction is changed at the reflection. The first polarized reflected light and the second polarized reflected light may be orthogonal to each other with respect to polarization directions thereof. The second measurement light reflected from the test substance may include third polarized reflected light (SS) whose polarization direction is maintained during fundus reflection, and fourth polarized reflected light (SP) whose polarization direction is changed during the reflection. In a case where the optical delay path is used, for example, the first polarized reflected light and the second polarized reflected light may have optical path length differences from the third polarized reflected light and the fourth polarized reflected light.

Regarding the detector, a single detector or a plurality of detectors may detect polarized reflected light. In a case of using a plurality of detectors, a first detector may detect the first polarized reflected light (PP) and the third polarized reflected light, and a second detector may detect the second polarized reflected light (PS) and the fourth polarized reflected light (SP).

The polarized light generator and the detector may match each other in that two light beams having different polarization components are generated and are detected. For example, the generator generates linearly polarized light beams which are orthogonal to each other, and the detector detects the linearly polarized light beams which are orthogonal to each other. The generator may generate circularly polarized light beams which are orthogonal to each other, and the detector may detect, for example, the linearly polarized light beams which are orthogonal to each other. Polarization directions in the generator and the detector may not necessarily match each other.

Two polarization states P1 and P2 may be acquired by using the depth information based on the multiplex spectral signal. The polarization state P1 may be acquired based on depth information based on the first polarized reflected light (PP) and depth information based on the second polarized reflected light (PS). The polarization state P2 may be acquired based on depth information based on the third polarized reflected light (SS) and depth information based on the fourth polarized reflected light (SP).

<Irradiation with at Least Two Beams>

The light guide optical system may include a scanning optical system which scans different positions on a test substance with the first measurement light and the second measurement light into which light is split by the second light splitter. In other words, the measurement light may be split into two beams which are separate from each other via the second light splitter. The optical path length difference generator may provide an optical path length difference to one of the two separate beams. Different parts may be simultaneously irradiated with the respective beams, and thus the test substance may be scanned with the beams by the optical scanner.

The controller may process an output signal which is output from the detection optical system so as to acquire a first tomographic image formed by a first beam and a second tomographic image formed by a second beam. In a case where an optical path length difference is provided, the optical path length difference may be set so that a tomographic image formed by one beam is formed on the front side, and a tomographic image formed by the other beam is formed on the rear side, in an imaging range of the tomographic images in the depth direction.

The scanning optical system may perform scanning with two beams in directions in which the two beams are split, for example, during scanning once, so that the same position on the test substance is scanned with the respective beams.

The controller may process an output signal from the detection optical system so as to acquire at least two tomographic images whose acquisition times are different from each other at the same part and to acquire motion contrast data regarding the same part.

The scanning optical system of the OCT apparatus 1 performs scanning with two beams in directions which are different from a split direction of each beam, for example, during scanning once so as to scan different positions on the test substance with the respective beams. The controller may process an output signal from the detection optical system so as to acquire a first tomographic image and a second tomographic image regarding different scanning positions.

<Optical Coupler (See FIGS. 3 and 4)>

A light guide optical system may includes an optical coupler (for example, a polarized beam coupler 303 which is configured to couple a first measuring light and a second measuring light which are split by the second optical splitter, and is arranged between the second optical splitter and the test substance. In this case, the optical coupler may be an optical coupler configured to pass the first measurement light and reflect the second measurement light.

The optical coupler may couple the first measurement light and the second measurement light which are directed to the test substance, and divide a light reflected from the test substance due to the first measurement light and a light reflected from the test substance due to the second measurement light. The reflected lights divided by the optical coupler may be guided to the second optical splitter.

An optical deflector (for example, optical deflector 305) configured to change the permeation rate of one of the first measurement light and the second measurement light may be arranged between the second optical splitter and the optical coupler. The separation state of the first measurement light and the second measurement light can be controlled by driving the optical deflector. In this case, the first measurement light and the second measurement light may be adjusted to be coaxial, or the first measurement light and the second measurement light can be adjusted to be separated from each other. Further, the separation amount of the first measurement light and the second measurement light can be adjusted.

Figure 3:
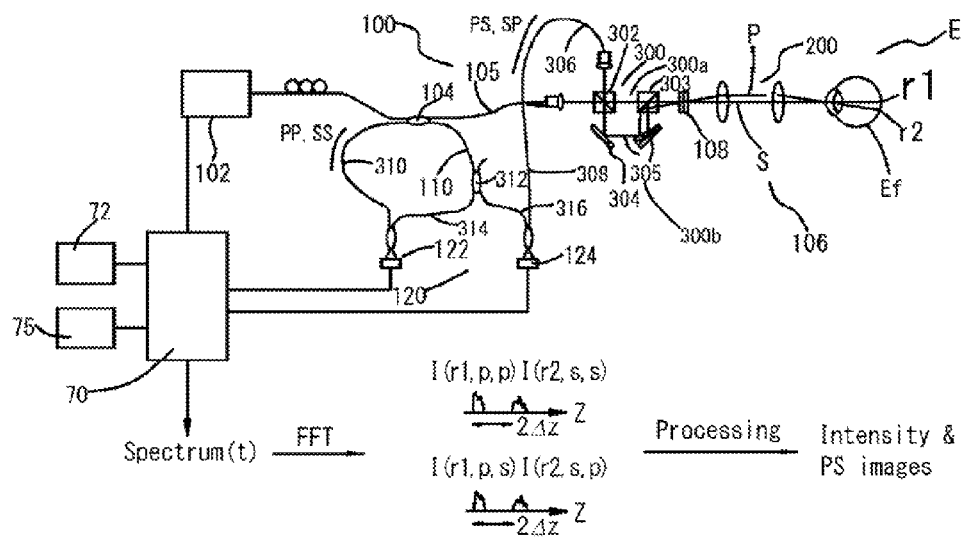
FIG. 3 is a diagram for explaining an apparatus configuration according to the present embodiment.

In this case, for example, the separation state of the first measurement light and the second measurement light can be controlled by changing the traveling direction of the measurement light by driving the optical deflector (see FIG. 3). In this case, for example, incident angles of the first measurement light and the second measurement light entering a scanning optical system may be set at different angles so that the first measurement light and the second measurement light may be scanned by the scanning optical system while they have a certain angle difference to change the traveling angle of the first measurement light and the second measurement light. The traveling angle of the first measurement light and the second measurement light may be adjusted by a reflection mirror, for example.

Figure 4:
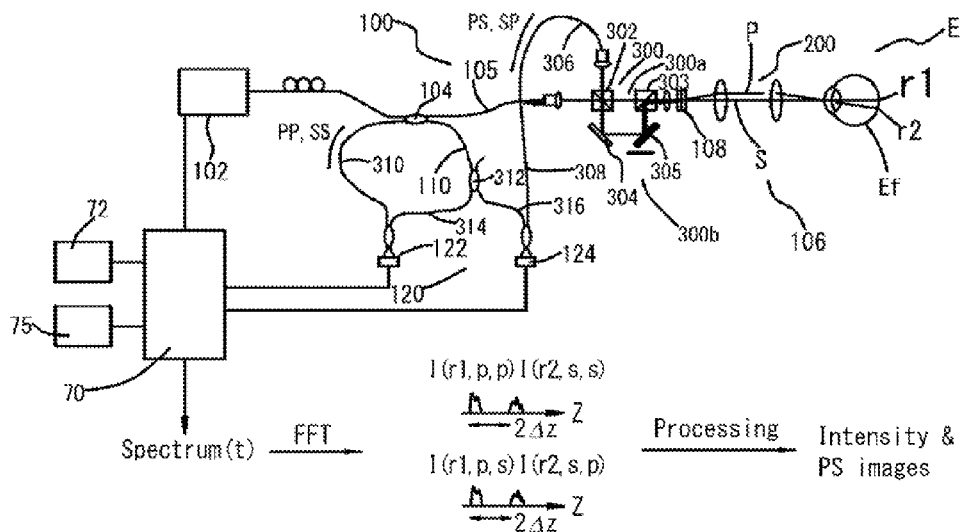
FIG. 4 is a diagram for explaining an apparatus configuration according to the present embodiment.

For example, the separation state of the first measurement light and the second measurement light can be controlled by parallel moving the traveling positions of the first measurement light and the second measurement light by driving the optical deflector (see FIG. 4). The parallel movement of the first measurement light and the second measurement light can be performed by sliding the reflection mirror. In this case, the lens may be arranged between the scanning optical system and the optical coupler.

<Calibration>

In the present apparatus, at least some of the measurement optical path, the reference optical path, and the detection optical system may be formed of a fiber optical system. Here, when polarization characteristics of the test substance are analyzed, the calculation controller may perform calibration on a polarization component caused by the fiber optical system by using a measurement result for a known calibration sample.

This calibration process is also applicable to optical systems other than the above-described optical systems as long as the optical systems employ a fiber-based PS-OCT.

EXAMPLE

In Example, an OCT apparatus 1 illustrated in FIG. 1 is used as the optical coherence tomography (OCT) apparatus. The test substance may be a fundus of the eye. The apparatus of Example may have a configuration in which polarization components which are orthogonal to each other may be detected by different detectors.

The OCT apparatus 1 may have a swept source OCT (SS-OCT) as a basic configuration, and may include a wavelength variable light source 102, an OCT optical system (interference optical system) 100, and a calculation controller (hereinafter, referred to as a controller) 70. The OCT apparatus 1 may be additionally provided with a memory 72, a monitor 75, and a front image observation system and a fixation target projection system (not illustrated). The controller 70 may be connected to the wavelength variable light source 102, the OCT optical system 100, the memory 72, and the monitor 75.

The OCT optical system 100 may employ an SS-OCT system. As the light source 102, a wavelength variable light source (wavelength scanning type light source) which changes an emission wavelength temporally at a high speed may be used. The light source 102 is constituted of, for example, a laser medium, a resonator, and a wavelength selection filter. Examples of the wavelength selection filter may include a combination of a diffraction grating and a polygon mirror, and a filter using Fabry-Perot etalon.

In the present embodiment, as a light source in which an instantaneous emission line width is small, and a resonator length is short, TUNABLE LASER manufactured by AXSUN Technologies LLC may be used (for example, $\lambda c=1060$ nm, $\Delta\lambda=110$ mm, $\delta\lambda=0.055$ nm, and the resonator length=14 mm). Such a wavelength variable light source is disclosed in, for example, U.S. Patent Publication No. 2009/0059971.

The coupler (splitter) 104 may be used as a light splitter and may split light emitted from the light source 102 into measurement light (also referred to as sample light) and reference light. Here, the measurement light reaches the optical delay path 300 via an optical fiber 105. The coupler 104 may be a circulator.

The OCT optical system 100 guides the measurement light to a fundus Ef of the eye E via a measurement optical system 106. The OCT optical system 100 guides the reference light to the reference optical system 110. The OCT optical system 100 receives interference between the measurement light reflected from the fundus Ef and the reference light by using the detector (light receiving element) 120.

The measurement optical system 106 may include, for example, the optical delay path 300, an optical scanner 108, and a light guide optical system 200. The optical delay path 300 may include a standard optical path 300a and a bypass optical path 300b, and may be provided to generate at least two measurement light beams having optical path length differences from each other. For example, in a case where the optical delay path 300 is disposed on the measurement optical path, at least two light beams having optical path length differences from each other are formed by the standard optical path 300a and the bypass optical path 300b. The bypass optical path 300b has a longer optical path length than the standard optical path 300a, and thus measurement light passing through the bypass optical path 300b is subject to optical delay (optical path length difference) relative to measurement light passing through the standard optical path.

The optical delay path 300 is provided with a polarized beam splitter 302 and a light reflection member 304. The optical delay path 300 may divide an optical path of the measurement light into two optical paths so that one measurement light beam may be delayed relative to the other measurement light beam. The polarized beam splitter 302 divides an optical path of the measurement light from the optical fiber 105 into the standard optical path 300a (first measurement optical path) and the bypass optical path 300b (second measurement optical path). Hereinafter, regarding the measurement light, light passing through the standard optical path 300a is referred to as first measurement light (P), and light passing through the bypass optical path 300b is referred to as second measurement light (S). In other words, the polarized beam splitter 302 divides light from the optical fiber 105 into the first measurement light and the second measurement light.

The polarized beam splitter 302 may divide the light from the optical fiber 105 into polarization components which are orthogonal to each other. In other words, the first measurement light and the second measurement light may have a relationship of being orthogonal to each other with respect to the polarization components. The polarized beam splitter 302 may have a characteristic of transmitting one polarization component therethrough, and reflecting the other polarization component. As a result, the subject's eye is irradiated with the measurement light of which the polarization components are orthogonal to each other by the polarized beam splitter 302.

Here, the first measurement light is directed toward the eye E via the optical scanner 108 and the light guide optical system 200. The second measurement light is directed toward the eye E via the light reflection member 304, the optical scanner 108, and the light guide optical system 200. The light reflection member 304 may be disposed so that a principal ray of the second measurement light intersects a principal ray of the first measurement light.

The light reflection member 304 may be an optical member such as a total reflection mirror or a prism. Optical members forming the optical delay path 300 may have an optical arrangement of being separated from each other as illustrated in FIG. 1, and may have an optical arrangement of being integrated by a prism or the like.

Reflection directions of the first measurement light and the second measurement light may be changed by the optical scanner 108. The light deflected by the optical scanner 108 is converted into parallel light by the light guide optical system 200, and is incident to the eye E so as to be applied to the fundus Ef.

The optical scanner 108 may scan the fundus Ef with the measurement light in XY directions (crossing directions).

The optical scanner 108 is disposed at a position substantially conjugate to the pupil. The optical scanner 108 is constituted of, for example, two galvano mirrors, and reflection angles thereof are arbitrarily adjusted by a driving mechanism.

Consequently, reflection (traveling) directions of light beams emitted from the light source 102 are changed by the optical scanner 108, and the fundus is scanned with the light beams at any position. For example, not only a reflective mirror (a galvano mirror, a polygon mirror, or a resonant scanner) but also an acousto-optical element (AOM) which changes a traveling (deflection) direction of light may be used as the optical scanner 108.

Here, the principal ray of the first measurement light and the principal ray of the second measurement light intersect each other at the pupil conjugate position (optical scanner), and thus the first measurement light and the second measurement light temporarily intersect each other on the pupil and then reach the fundus Ef. The first measurement light P and the second measurement light S are separated spatially from each other with an appropriate gap Δ in the scanning direction. As mentioned above, two probe beams formed of the first measurement light P and the second measurement light S are formed with the gap Δ in the scanning direction. In FIG. 1, r1 indicates an irradiation position of the first measurement light P, and r2 indicates an irradiation position of the second measurement light S.

The controller 70 may control driving the optical scanner 108 so as to apply the first measurement light and the second measurement light in a direction (crossing direction) which is perpendicular to the depth direction of the fundus Ef. The first measurement light and the second measurement light may be separated from each other in the scanning direction. The controller 70 may adjust a scanning direction of the optical scanner 108 so that the first measurement light and the second measurement light are simultaneously applied to different positions on the same scanning line on the fundus.

Here, reflected light beams (scattered light beams) of the first measurement light P and the second measurement light S from the fundus Ef reach the optical delay path 300 via the light guide optical system 200 and the optical scanner 108. The first measurement light P reflected from the fundus reaches the polarized beam splitter 302 via the light guide optical system 200, the optical scanner 108, and the standard optical path 300a. The second measurement light S reflected from the fundus reaches the polarized beam splitter 302 via the light guide optical system 200, the optical scanner 108, and the bypass optical path 300b.

The polarized beam splitter 302 may split the first measurement light reflected from the fundus. The polarized beam splitter 302 returns one first measurement light beam to the optical fiber 105 and also newly guides the other first measurement light beam to an optical fiber 306. Thereafter, one first measurement light beam is directed toward the optical fiber 105, the coupler 104, and an optical fiber 310.

The polarized beam splitter 302 may split the first measurement light reflected from the fundus into polarization components which are perpendicular to each other. Here, the first measurement light reflected from the fundus includes first polarized reflected light (PP) whose polarization direction is maintained during fundus reflection, and second polarized reflected light (PS) whose polarization direction is changed during the fundus reflection. The first polarized reflected light and the second polarized reflected light are orthogonal to each other with respect to the polarization directions. The second polarized reflected light has the same polarization component as that of the second measurement light before being applied to the fundus. The polarized beam splitter 302 returns, for example, the first polarized reflected light to the optical fiber 105, and also newly guides the second polarized reflected light to the optical fiber 306.

The polarized beam splitter 302 may split the second measurement light reflected from the fundus. The polarized beam splitter 302 returns one second measurement light beam to the optical fiber 105, and also newly guides the other second measurement light beam to the optical fiber 306. Thereafter, one second measurement light beam is directed toward the optical fiber 105, the coupler 104, and the optical fiber 310.

The polarized beam splitter 302 may split the second measurement light reflected from the fundus into polarization components which are perpendicular to each other. Here, the second measurement light reflected from the fundus includes third polarized reflected light (SS) whose polarization direction is maintained during fundus reflection, and fourth polarized reflected light (SP) whose polarization direction is changed during the fundus reflection. The third polarized reflected light and the fourth polarized reflected light are orthogonal to each other with respect to the polarization directions. The fourth polarized reflected light has the same polarization component as that of the first measurement light before being applied to the fundus. The polarized beam splitter 302 returns, for example, the third polarized reflected light to the optical fiber 105, and also newly guides the fourth polarized reflected light to the optical fiber 306.

Here, the polarized beam splitter 302 has a characteristic of reflected light with respect to polarization components which are orthogonal to each other. Therefore, the first polarized reflected light PP and the third polarized reflected light SS are directed toward the optical fiber 105, and the second polarized reflected light PS and the fourth polarized reflected light SP are directed toward the optical fiber 306. The third polarized reflected light SS has optical delay (optical path length difference) relative to the first polarized reflected light PP. The fourth polarized reflected light SP has optical delay (optical path length difference) relative to the second polarized reflected light PS. The reflected light beams (the first polarized reflected light PP, the second polarized reflected light PS, the third polarized reflected light SS, and the fourth polarized reflected light SP) acquired due to reflection of the measurement light on the fundus Ef are combined with the reference light so as to interfere therewith.

The reference optical system 110 generates reference light which is combined with fundus reflected light based on measurement light. The reference optical system 110 may include a light splitter 312 which splits the reference light into reference light beams. Regarding the reference light beams as a result of splitting in the light splitter 312, one reference light beam is directed toward an optical fiber 314, and the other reference light beam is directed toward an optical fiber 316.

The reference optical system 110 may be of a Michelson type, and may be of a Mach-Zenhder type. As another example, the reference optical system 110 is constituted of a transmission optical system (for example, an optical fiber), and transmits light from the coupler 104 without returning the light so that the light is guided to the detector 120. The reference optical system 110 is constituted of, for example, a reflection optical system (for example, a reference mirror), and reflects light from the coupler 104 with the reflection optical system so that the light is returned to the coupler 104 and is thus guided to the detector 120.

The present apparatus may include an adjuster (optical path length difference changing unit) which adjusts an optical path length difference between measurement light and reference light. The adjuster may include an actuator which changes an optical path length of at least one of the measurement light and the reference light. For example, the adjuster adjusts an optical path length difference by moving at least some of the optical members disposed in the OCT optical system 100 in the optical axis direction. For example, the adjuster may be disposed in the reference optical system 110, and may adjust an optical path length difference between the measurement light and the reference light by moving the optical members on the reference light. A configuration for adjusting an optical path length difference may be disposed on the measurement optical path. For example, the optical member (for example, an end of the optical fiber) disposed on the measurement optical path may be moved in the optical axis direction.

The detector 120 may include a first polarized light detector 122 and a second polarized light detector 124. The first polarized light detector 122 and the second polarized light detector 124 may respectively detect interference of polarization components which are orthogonal to each other.

Each of the first polarized light detector 122 and the second polarized light detector 124 may be a balanced detector formed of a first light receiving element and a second light receiving element. The balanced detector can reduce unnecessary noise included in interference signals by obtaining an interference signal from the first light receiving element and an interference signal from the second light receiving element. Each light receiving element may be a point sensor in which only a single light emitting portion is provided, and, for example, an avalanche photodiode is used.

Interference signal light received by the first polarized light detector 122 and the second polarized light detector 124 includes interference signal light beams corresponding to two measurement light beams whose polarization components are orthogonal to each other and which have optical path length differences from each other.

If an emission wavelength is changed by the light source 102, interference signal light corresponding thereto is received by the detector 120, and is thus detected as a spectral signal by the detector 120.

The respective spectral signals detected by the first polarized light detector 122 and the second polarized light detector 124 include a first spectral signal formed based on the first measurement light of the first measurement light and the second measurement light applied to the fundus, and a second spectral signal formed based on the second measurement light whose polarization component is orthogonal thereto. The first spectral signal and the second spectral signal have optical path length differences from each other, and thus differ in the density of interference fringes formed by spectra.

More specifically, the first polarized light detector 122 detects a spectral signal formed based on the first polarized reflected light PP and a spectral signal formed based on the third polarized reflected light SS. The second polarized light detector 124 detects a spectral signal formed based on the second polarized reflected light PS, and a spectral signal formed based on the fourth polarized reflected light SP.

The controller 70 processes the respective spectral signals detected by the first polarized light detector 122 and the second polarized light detector 124 so as to obtain depth information regarding polarization components which are orthogonal to each other.

More specifically, the controller 70 obtains first depth information I(r1,p,p) and third depth information I(r2,s,s) based on the spectral signal detected by the first polarized light detector 122. The first depth information I(r1,p,p) is depth information based on a spectral signal of the first polarized reflected light PP, and the third depth information I(r2,s,s) is depth information based on the third polarized reflected light SS. For example, I(r1,p,p) indicates depth information formed by the first polarized reflected light PP from an irradiation position r1.

The controller 70 obtains the second depth information I(r1,p,s) and the fourth depth information I(r2,s,p) based on the spectral signal detected by the second polarized light detector 124. The second depth information I(r1,p,s) is depth information based on a spectral signal of the second polarized reflected light PS, and the fourth depth information I(r2,s,p) is depth information based on the fourth polarized reflected light SP.

<Acquisition of Tomographic Image>

The controller 70 controls driving of the optical scanner 108 so as to scan the fundus Ef with measurement light in the crossing direction. The controller 70 arranges depth information pieces at the respective scanning positions so as to form a fundus tomographic image.

Figure 2A:
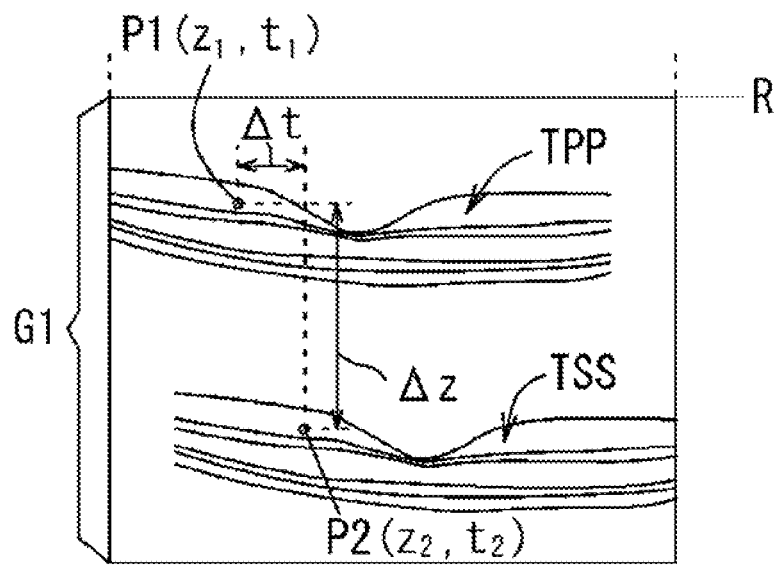
FIG. 2A illustrates an example of tomographic image data acquired by a first polarized light detector according to the present embodiment.
Figure 2B:
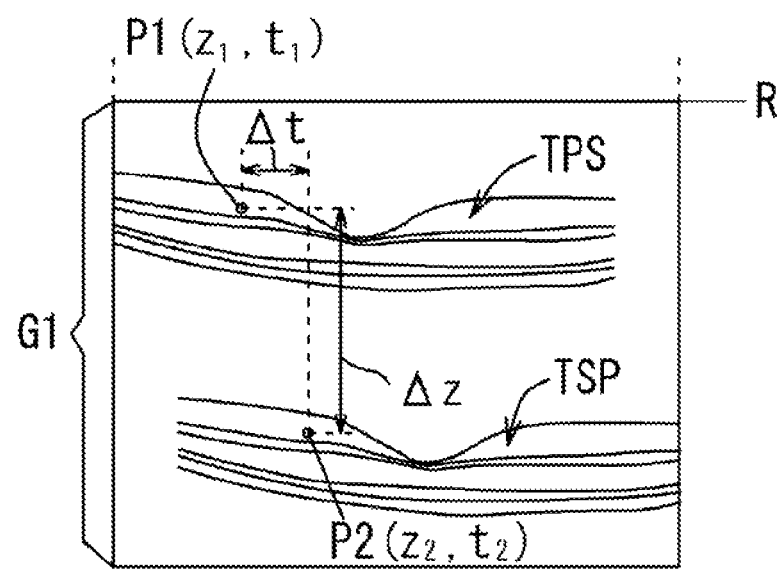
FIG. 2B illustrates an example of tomographic image data acquired by a second polarized light detector according to the present embodiment.

FIGS. 2A and 2B illustrate examples of tomographic image data which is acquired based on a multiplex spectral signal, in which FIG. 2A illustrates tomographic image data acquired by the first polarized light detector, and FIG. 2B illustrates tomographic image data acquired by the second polarized light detector. Tomographic image data acquired through Fourier analysis includes a real image and a mirror image (imaginary image), but FIGS. 2A and 2B illustrate images obtained by extracting only the real image.

The controller 70 may arrange depth information pieces regarding polarization components which are orthogonal to each other, in the scanning direction. Consequently, first tomographic image data and the second tomographic image data regarding the polarization components which are orthogonal to each other may be obtained. Each item of the tomographic image data includes a plurality of tomographic images of the fundus Ef which are separated from each other in the depth direction. The tomographic image data may be formed, for example, by obtaining absolute values of real and imaginary components in each piece of depth information.

The first tomographic image data includes a first tomographic image TPP based on first depth information and third tomographic image TSS based on third depth information, and is generated based on an output signal from the first polarized light detector 122. The second tomographic image data includes a second tomographic image TPS based on second depth information and a fourth tomographic image TSP based on fourth depth information, and is generated based on an output signal from the second polarized light detector 124.

The controller 70 may extract at least one of the first tomographic image TPP, the second tomographic image TPS, the third tomographic image TSS, and the fourth tomographic image TSP from the first tomographic image data and the second tomographic image data, and may display the extracted tomographic image on a screen of the monitor 75. The controller 70 may continuously acquire the first tomographic image data and the second tomographic image data so as to display tomographic images as moving images.

<Optical Path Length Difference ΔZ, and Shift Amount Δt in Horizontal Direction>

In an imaging region G1 in each piece of the tomographic image data, the first tomographic image TPP and the second tomographic image TPS may be formed in a front region, and the third tomographic image TSS and the fourth tomographic image TSP may be formed in a rear region. A difference between imaging positions in the depth direction is caused by an optical path length difference between the first measurement light and the second measurement light.

The first tomographic image TPP and the second tomographic image TPS are formed in a state of being shifted in the horizontal direction (scanning direction) relative to the third tomographic image TSS and the fourth tomographic image TSP. In other words, depth information pieces corresponding to the same imaging part are deviated in the horizontal direction. A difference between imaging positions in the horizontal direction is caused by a difference between irradiation positions of the first measurement light and the second measurement light.

For example, in FIG. 2A, a point P1 ($z_1, t_1$) on the first tomographic image TPP and a point P2 ($z_2, t_2$) on the third tomographic image TSS are related to the same part in the depth direction and the horizontal direction. A shift amount Δz of a tomographic image in the depth direction corresponds to an optical path difference between the first measurement light and the second measurement light, and is known in advance. For example, the shift amount Δz is calculated in the pixel unit. A relationship of $z_2 = z_1 + \Delta z$ is established.

A shift amount Δt of a tomographic image in the horizontal direction corresponds to a difference between irradiation positions of the first measurement light and the second measurement light, and is known in advance. For example, the shift amount Δt is calculated in the pixel unit. A relationship of $t_2 = t_1 + \Delta t$ is established. The shift amount Δt may be obtained through optical simulation, and may be obtained based on a deviation amount between the first tomographic image and the second tomographic image in the tomographic image data.

<Acquisition of Addition Average Image>

The controller 70 may acquire an addition average image by using at least two tomographic images included in the first tomographic image data and the second tomographic image data. For example, the controller 70 extracts the first tomographic image TPP and the third tomographic image TSS from the first tomographic image data. The controller 70 may perform positioning between the images through image processing so as to acquire an addition average image. Of course, the controller 70 may acquire an addition average image based on two tomographic images in the second tomographic image data. The controller 70 may acquire an addition average image by using a tomographic image in the first tomographic image data and a tomographic image in the second tomographic image data.

In the above-described way, it is possible to acquire an addition average image in which speckle noise is neutralized within a short period of time. The controller 70 may continuously acquire the first tomographic image data and the second tomographic image data, and may process a plurality of tomographic images included in the tomographic image data acquired in a time series so as to obtain an addition average image. Consequently, it is possible to acquire a more favorable image within a short period of time. In a case where an addition average image is obtained, the controller 70 may acquire the addition average image by using real and imaginary components in the Z space which is a basis of each tomographic image.

<Acquisition of Fundus Angiographic Image (OCT Motion Contrast Image)>

The controller 70 may acquire a motion contrast image based on tomographic images of at least two frames in which acquisition times of spectral signals are different from each other at the same part. For example, the controller 70 may obtain a phase change amount at points corresponding to the same part based on the first tomographic image TPP and the third tomographic image TSS in the first tomographic image data. The controller 70 may obtain a phase change amount at points corresponding to the same part based on the second tomographic image TPS and the fourth tomographic image TSP in the second tomographic image data. Of course, the controller 70 may obtain a phase change amount by using the tomographic image in the first tomographic image data and the tomographic image in the second tomographic image data.

For example, a phase $\Phi_1$ ($z_1, t_1$) and a phase $\Phi_2$ ($z_2, t_2$) on the point P1 ($z_1, t_1$) and the point P2 ($z_2, t_2$) are expressed in this order as follows.

[Expression 1]

$$\Phi_{1,n}(z_1, t_1) = \arctan\left(\frac{Im(\tilde{I}_{1,n}(z_1))}{Re(\tilde{I}_{1,n}(z_1))}\right),$$

$$\Phi_{2,n}(z_2, t_2) = \Phi_{1,n}(z + \Delta z, t + \Delta t)$$
$$= \arctan\left(\frac{Im(\tilde{I}_{2,n}(z_2, t_2))}{Re(\tilde{I}_{2,n}(z_2, t_2))}\right)$$
$$= \arctan\left(\frac{Im(\tilde{I}_{1,n}(z + \Delta z, t + \Delta t))}{Re(\tilde{I}_{1,n}(z + \Delta z, t + \Delta t))}\right)$$

[Expression 2]

$$\tilde{I}_{1,n}(z)$$

Expression 2 indicates complex scattering intensity obtained by performing FFT on spectra with respect to the wave number k.

$$I_{1,n}(z) \quad \text{[Expression 3]}$$

The normal OCT intensity as indicated in Expression 3 has a relationship as expressed in Expression 4.

$$I_{1,n}(z) = \sqrt{(Re(\tilde{I}_{1,n}(z)))^2 + (Im(\tilde{I}_{1,n}(z)))^2} \quad \text{[Expression 4]}$$

Here, Im indicates an imaginary part of a complex number, and Re indicates a real part of the complex number. In addition, n is set to 1 to N−1, and indicates that a single point is measured through an A scan for N times.

A phase change ΔΦ (z, Δt) is expressed as in Expression 5.

$$\Delta\Phi_n(z, \Delta t) = \Phi_{1,n}(z_1, t_1) - \Phi_{2,n}(z_2, t_2) + \Phi_0 \quad \text{[Expression 5]}$$

Here, $\Phi_0$ indicates motion of the entire sample or an initial phase difference.

In the above-described way, the controller 70 may acquire a profile regarding a phase difference of a complex OCT signal in the depth direction, and may add gradations to the profile according to a size thereof so as to acquire a motion contrast image. A blood flow speed may be calculated based on the calculated phase difference and a direction of a blood vessel.

The controller 70 may control driving of the optical scanner 108 so as to obtain three-dimensional motion contrast data by scanning the fundus Ef with the measurement light in a two-dimensional manner. The controller 70 may obtain motion contrast data at each position so as to acquire a two-dimensional motion contrast front image (En-face image) on a fundus plane. The controller 70 displays the obtained front image on the monitor 75.

A method of calculating a motion contrast based on a complex OCT signal is not limited to the above-described method. For example, there may be a method of calculating a vector difference of a complex OCT signal, and a method of multiplying a phase difference and a vector difference of a complex OCT signal by each other.

<Polarized Light Detection>

The controller 70 may obtain characteristics of birefringence characteristics of the fundus Ef based on the above-described first depth information to fourth depth information. In this case, information regarding a real part and an imaginary part in each piece of the depth information is used.

More specifically, the controller 70 obtains a first polarization state based on the first depth information and the second depth information. The first depth information and the second depth information are depth information based on the first measurement light P, and polarization components thereof are orthogonal to each other. The controller 70 obtains a second polarization state based on the third depth information and the fourth depth information. The third depth information and the fourth depth information are depth information based on the second measurement light S, and polarization components thereof are orthogonal to each other.

The controller 70 obtains birefringence characteristics at a position of the fundus Ef with a fundus surface as a reference based on the first polarization state and the second polarization state. The controller 70 obtains the birefringence characteristics in the depth direction so as to obtain polarization depth information indicating a birefringence characteristic distribution of the fundus Ef in the depth direction.

The controller 70 arranges polarization depth information pieces at respective positions so as to obtain a birefringence distribution (for example, a polarization depth information image) of the fundus Ef in a certain section. The controller 70 displays the obtained birefringence distribution on the monitor 75.

The controller 70 may control driving of the optical scanner 108 so as to obtain three-dimensional data by scanning the fundus Ef with the measurement light in a two-dimensional manner. The controller 70 obtains polarization depth information at each position so as to obtain a map indicating a two-dimensional birefringence distribution on the fundus Ef. The controller 70 displays the obtained map on the monitor 75.

As a specific method of obtaining polarization information, for example, there may be a method (for example, refer to B. Hyle Park, M. C. Pierce, Barry Cense, S. H Yun, B. E. Bouma, J. F. de Boer, "Real-time fiber-based multi-functional spectral domain optical coherence tomography at 1.3 µm", Optics Express, Vol 13 ('05), pp. 3931 to 3944) using Stokes parameters, and a method (for example, refer to JP-A-2007-298461) using a Jones vector. In addition, as a method of obtaining polarization information based on a multiplex spectral signal, refer to, for example, JP-A-2013-148482.

According to one aspect of the present embodiment, a first light splitter (for example, the coupler 104) splits an optical path of light from a light source (for example, the light source 102) into a first optical path (for example, the optical fiber 105) and a reference optical path (for example, the reference optical system 110). A second light splitter (for example, the polarized beam splitter 302) splits light from the first optical path (for example, the optical fiber 105) into the first measurement light P and the second measurement light S, and also splits optical paths of fundus reflected light based on the first measurement light P and fundus reflection light based on the second measurement light S into the first optical path and a second optical path (for example, the optical fiber 306). A first light detector (for example, the first polarized light detector 122) detects first interference which is interference between the fundus reflection light having passed through the first optical path and reference light having passed through the reference optical path. A second light detector (for example, the second polarized light detector 124) detects second interference which is interference between the fundus reflection light having passed through the second optical path and the reference light having passed through the reference optical path. Consequently, in the OCT optical system, the fundus reflection light is effectively used, and thus a light amount loss of the fundus reflection light is improved.

According to another aspect of the present embodiment, a polarized beam splitter (for example, the polarized beam splitter 302) splits light from an OCT light source into polarization components which are orthogonal to each other, and also splits light from the fundus into polarization components which are orthogonal to each other. Consequently, it is not necessary to provide polarized beam splitters in both a light transmission system and a light reception system. As a result, it is possible to simplify an apparatus configuration of the PS-OCT which tends to be complex. The polarized beam splitter is not necessarily used, and, for example, in a case where the present embodiment is not applied to the PS-OCT, a light splitter such as a half mirror may be used instead of the polarized beam splitter 302.

According to still another aspect of the present embodiment, an optical delay path (for example, the optical delay path 300) delays an optical path length of one of the first measurement light and the second measurement light as a result of splitting in the second light splitter relative to an optical path length of the other measurement light. Consequently, when OCT data is obtained, OCT data (for example, the first depth information and the second depth information) based on the first measurement light and OCT data (for example, the third depth information and the fourth depth information) based on the second measurement light are separated from each other in the depth direction. Consequently, it is possible to perform an analysis process based on each piece of the OCT data.

Modification Examples

In the above description, the first light detector and the second light detector are configured separately from each other, but this is only an example. For example, in the OCT optical system, a single light detector may be configured to detect the first interference and the second interference. In this case, respective pieces of OCT data may be separated from each other by providing an optical path length difference between the first optical path and the second optical path. In this case, four pieces of OCT data which are separated from each other in the depth direction are detected. Therefore, in order to secure an imaging range in the depth direction, a wavelength variable light source whose imaging range is wide, a full-ranging technique, or the like may be used.

In the above description, light beams as a result of splitting in the first light splitter may be guided to the first optical path and the second optical path. In this case, the second light splitter may split the light from the second optical path into the first measurement light P and the second measurement light S, and may also split optical paths of fundus reflection light based on the first measurement light P and fundus reflection light based on the second measurement light S into the first optical path and the second optical path. There may be a configuration in which a bypass optical path is not provided. In this case, the second light splitter may generate the first measurement light P based on light from the first optical path, and may generate the second measurement light S based on light from the second optical path. The second light splitter may split optical paths of fundus reflection light based on the first measurement light P and fundus reflection light based on the second measurement light S into the first optical path and the second optical path.

In the above description, the first measurement light P and the second measurement light S are applied to different positions on the fundus, but this is only an example. For example, the OCT optical system may have a configuration in which the first measurement light P and the second measurement light S are applied to the same position on the fundus. A light coupler (for example the polarized beam splitter 303) which couples the first measurement light P and the second measurement light S obtained as a result of splitting in the second light splitter, with each other, may be provided between, for example, the optical scanner and the second light splitter.

In the above description, the OCT optical system is built based on a fiber optical system but is not limited thereto, and may be built based on a bulk optical system. In the above description, the configuration illustrated as a bulk optical system may be built by a fiber optical system.

<Calibration>

Hereinafter, a description will be made of specific examples of calibration. The calibration may be used to correct deviation in an inherent polarization component between the measurement optical path and the reference optical path in a case where at least one of the measurement optical path and the reference optical path is built by fibers. As in the embodiment, the calibration is also used to correct deviation in such a polarization component in a case where a plurality of measurement optical paths are provided (a plurality of reference optical paths may be provided). In the above-described manner, when polarization characteristics of a test substance are obtained, errors caused by influence specific to the apparatus can be reduced, and thus the polarization characteristics can be specified with high accuracy.

A Jones vector of measurement light which comes out of the fiber 105 and is then emitted from the polarized beam splitter 302 is expressed as follows when amplitude is indicated by $E_{samp}$, a wave number is indicated by k, an optical path length difference between two light beams including p-polarized light and s-polarized light is indicated by δ, and an intensity difference is indicated by γ.

[Expression 6]

$$\vec{E}_p = E_{samp}\begin{pmatrix}1\\0\end{pmatrix}, \vec{E}_s = \gamma E_{samp}\begin{pmatrix}0\\e^{ik\delta}\end{pmatrix} \qquad \text{Equation 1}$$

A Jones matrix of double paths of a test substance is expressed as Equation 2.

[Expression 7]

$$J_{samp} = \begin{pmatrix}J_{11} & J_{12}\\J_{21} & J_{22}\end{pmatrix} \qquad \text{Equation 2}$$

In this case, two light beams after being scattered (reflected) on the test substance and right before being incident to the polarized beam splitter 302 are expressed as follows.

[Expression 8]

$$\begin{cases}\vec{E}'_p = J_{samp}\vec{E}_p e^{2ikz_1} = E_{samp}e^{2ikz_1}\begin{pmatrix}J_{11}\\J_{21}\end{pmatrix}\\\vec{E}'_s = J_{samp}\vec{E}_s e^{2ikz_2} = \gamma E_{samp}e^{2ik(z_2+\delta)}\begin{pmatrix}J_{12}\\J_{22}\end{pmatrix}\end{cases} \qquad \text{Equation 3}$$

Here, $z_1$ and $z_2$ indicate scattering depths in the test substance.

Thereafter, a state right before a light beam which has passed through the polarized beam splitter 302 and is directed toward the detector 122 is incident to the fiber, and a state right before a light beam which has passed through the polarized beam splitter 302 and is directed toward the detector 124 is incident to the fiber, are respectively expressed as follows.

[Expression 9]

$$\begin{cases}\vec{E}_{samp,BD1} = E_{samp}\begin{pmatrix}J_{11}e^{2ikz_1}\\\gamma J_{22}e^{2ik(z_2+\delta)}\end{pmatrix}\\\vec{E}_{samp,BD2} = E_{samp}\begin{pmatrix}\gamma J_{12}e^{2ik(z_2+\delta)}\\J_{21}e^{2ikz_1}\end{pmatrix}\end{cases} \qquad \text{Equation 4}$$

Interference signals in the detector 122 and the detector 124 are computed by using the above Equations.

1). Interference Signal in Detector 122

A Jones matrix $JM_1$ from the polarized beam splitter 302 to the detector 122 is expressed as in Equation 5.

[Expression 10]

$$JM_1 = \begin{pmatrix}a_1 & b_1\\c_1 & d_1\end{pmatrix} \qquad \text{Equation 5}$$

In this case, interfering measurement light is expressed as follows.

[Expression 11]

$$\vec{E}'_{samp,BD1} = JM_1 \cdot \vec{E}_{samp,BD1}$$

$$= E_{samp}\begin{pmatrix} a_1 & b_1 \\ c_1 & d_1 \end{pmatrix}\begin{pmatrix} J_{11}e^{2ikz_1} \\ \gamma J_{22}e^{2ik(z_2+\delta)} \end{pmatrix} = E_{samp}\begin{pmatrix} a_1 J_{11}e^{2ikz_1} + b_1\gamma J_{22}e^{2ik(z_2+\delta)} \\ c_1 J_{11}e^{2ikz_1} + d_1\gamma J_{22}e^{2ik(z_2+\delta)} \end{pmatrix}$$

Equation 6

When amplitude is indicated by $E_{ref1}$, a reference light path length is indicated by $z_{ref1}$, and $\alpha_1$, $\beta_1$, and $\phi_1$ are real constant numbers, reference light in the detector 122 may be expressed as follows.

[Expression 12]

$$\vec{E}'_{ref,BD1} = \frac{E_{ref1}}{\sqrt{\alpha_1^2+\beta_1^2}}\begin{pmatrix} \alpha_1 \\ \beta_1 e^{i\phi_1} \end{pmatrix}e^{ikz_{ref1}}$$

Equation 7

Therefore, the interference intensity $I_{BD1}$ in the detector 122 is expressed as follows.

[Expression 13]

$$I_{BD1} \propto |\vec{E}'_{samp,BD1} + \vec{E}'_{ref1,BD1}|^2$$

$$= |\vec{E}'_{samp,BD1}|^2 + |\vec{E}'_{ref1,BD1}|^2 + E_{samp}\begin{pmatrix} a_1 J_{11}e^{2ikz_1} + b_1\gamma J_{22}e^{2ik(z_2+\delta)} \\ c_1 J_{11}e^{2ikz_1} + d_1\gamma J_{22}e^{2ik(z_2+\delta)} \end{pmatrix} \cdot \frac{E_{ref1}}{\sqrt{\alpha_1^2+\beta_1^2}}\begin{pmatrix} \alpha_1 \\ \beta_1 e^{-i\phi_1} \end{pmatrix}e^{-ikz_{ref1}} + c.c.$$

$$= |\vec{E}'_{samp,BD1}|^2 + |\vec{E}'_{ref1,BD1}|^2 + E_{samp}\frac{E_{ref1}}{\sqrt{\alpha_1^2+\beta_1^2}}\{(a_1\alpha_1 + c_1\beta_1 e^{-i\phi_1})e^{ik(2z_1-z_{ref1})}J_{11} + \gamma(b_1\alpha_1 + d_1\beta_1 e^{-i\phi_1})e^{ik(2z_2+2\delta-z_{ref1})}J_{22}\} + c.c.$$

$$\equiv |\vec{E}'_{samp,BD1}|^2 + |\vec{E}'_{ref1,BD1}|^2 + E_{samp}\frac{E_{ref1}}{\sqrt{\alpha_1^2+\beta_1^2}}\{(a_1\alpha_1 + c_1\beta_1 e^{-i\phi_1})e^{ik\cdot\Delta z_{11}}J_{11} + \gamma(b_1\alpha_1 + d_1\beta_1 e^{-i\phi_1})e^{ik(\Delta z_{12}+2\delta)}J_{22}\} + c.c.$$

Here, $\Delta z_{11} = 2z_1 - z_{ref1}$, and $\Delta z_{12} = 2z_2 - z_{ref1}$.

If Fourier transform is performed on the wave number k in Equation 8, an OCT signal is obtained as follows.

[Expression 14]

$$\tilde{I}_{BD1} \propto E_{samp}\frac{E_{ref1}}{\sqrt{\alpha_1^2+\beta_1^2}}\{(a_1\alpha_1 + c_1\beta_1 e^{-i\phi_1})J_{11}\cdot\delta(z-\Delta z_{11}) +$$
$$\gamma(b_1\alpha_1 + d_1\beta_1 e^{-i\phi_1})J_{22}\cdot\delta(z-(\Delta z_{12}+2\delta))\} + c.c.$$

Equation 9

2). Interference Signal in Detector 124

A Jones matrix $JM_2$ from the polarized beam splitter 302 to the detector 124 is expressed as in Equation 10.

[Expression 15]

$$JM_2 = \begin{pmatrix} a_2 & b_2 \\ c_2 & d_2 \end{pmatrix}$$

Equation 10

In this case, interfering measurement light is expressed as follows.

[Expression 16]

$$\vec{E}'_{samp,BD2} = JM_2 \cdot \vec{E}_{samp,BD2}$$

$$= E_{samp}\begin{pmatrix} a_2 & b_2 \\ c_2 & d_2 \end{pmatrix}\begin{pmatrix} \gamma J_{12}e^{2ik(z_1+\delta)} \\ J_{21}e^{2ikz_2} \end{pmatrix} = E_{samp}\begin{pmatrix} a_2\gamma J_{12}e^{2ik(z_1+\delta)} + b_2 J_{21}e^{2ikz_2} \\ c_2\gamma J_{12}e^{2ik(z_1+\delta)} + d_2 J_{21}e^{2ikz_2} \end{pmatrix}$$

Equation 11

When amplitude is indicated by $E_{ref2}$, a reference light path length is indicated by $z_{ref2}$, and $\alpha_2$, $\beta_2$, and $\phi_2$ are real constants, reference light in the detector 124 may be expressed as follows.

[Expression 17]

$$\vec{E}'_{ref,BD2} = \frac{E_{ref2}}{\sqrt{\alpha_2^2+\beta_2^2}}\begin{pmatrix} \alpha_2 \\ \beta_2 e^{i\phi_2} \end{pmatrix}e^{ikz_{ref2}}$$

Equation 12

Therefore, the interference intensity $I_{BD2}$ in the detector 124 is expressed as follows.

[Expression 18]

$$\begin{aligned}
I_{BD2} &\propto |\vec{E}'_{samp,BD2} + \vec{E}'_{ref2,BD2}|^2 \\
&= |\vec{E}'_{samp,BD2}|^2 + |\vec{E}'_{ref2,BD2}|^2 + E_{samp}\begin{pmatrix} a_2 J_{12} e^{2ik(z_1+\delta)} + b_2 J_{21} e^{2ikz_2} \\ c_2 J_{12} e^{2ik(z_1+\delta)} + d_2 \gamma J_{21} e^{2ikz_2} \end{pmatrix} \cdot \frac{E_{ref2}}{\sqrt{\alpha_2^2+\beta_2^2}} \begin{pmatrix} \alpha_2 \\ \beta_2 e^{-i\phi_2} \end{pmatrix} e^{-ikz_{ref2}} + c.c. \\
&= |\vec{E}'_{samp,BD2}|^2 + |\vec{E}'_{ref2,BD2}|^2 + E_{samp}\frac{E_{ref2}}{\sqrt{\alpha_2^2+\beta_2^2}} \{\gamma(a_2\alpha_2 + c_2\beta_2 e^{-i\phi_2})e^{ik(2z_1+2\delta-z_{ref2})}J_{12} + (b_2\alpha_2 + d_2\beta_2 e^{-i\phi_2})e^{ik(2z_2-z_{ref2})}J_{21}\} + \\
&\quad c.c. \\
&\equiv |\vec{E}'_{samp,BD2}|^2 + |\vec{E}'_{ref2,BD2}|^2 + E_{samp}\frac{E_{ref2}}{\sqrt{\alpha_2^2+\beta_2^2}} \{\gamma(a_2\alpha_2 + c_2\beta_2 e^{-i\phi_2})e^{ik(\Delta z_{21}+2\delta)}J_{12} + (b_2\alpha_2 + d_2\beta_2 e^{-i\phi_2})e^{ik\cdot\Delta z_{22}}J_{21}\} + c.c.
\end{aligned}$$

Equation 13

Here, $\Delta z_{21} = 2z_1 - z_{ref1}$, and $\Delta z_{22} = 2z_2 - z_{ref1}$.

If Fourier transform is performed on the wave number k in Equation 13, an OCT signal is obtained as follows.

[Expression 19]

$$\tilde{I}_{BD2} \propto E_{samp} \frac{E_{ref2}}{\sqrt{\alpha_2^2+\beta_2^2}}$$

$$\{\gamma(a_2\alpha_2 + c_2\beta_2 e^{-i\phi_2})J_{12} \cdot \delta(z - (\Delta z_{21} + 2\delta)) + (b_2\alpha_2 + d_2\beta_2 e^{-i\phi_2})J_{21} \cdot \delta(z - \Delta z_{22})\} + c.c.$$

Equation 14

From the above content, the OCT signal obtained in the detector 122 includes the following information.

[Expression 20]

$$\begin{cases} \Delta z_{11} & \cdots E_{samp} \dfrac{E_{ref1}}{\sqrt{\alpha_1^2+\beta_1^2}} (a_1\alpha_1 + c_1\beta_1 e^{-i\phi_1})J_{11} \equiv c1 \cdot J_{11} \\ \Delta z_{12} + 2\delta & \cdots E_{samp} \dfrac{E_{ref1}}{\sqrt{\alpha_1^2+\beta_1^2}} \gamma(b_1\alpha_1 + d_1\beta_1 e^{-i\phi_1})J_{22} \equiv c2 \cdot J_{22} \end{cases}$$

Equation 15

The OCT signal obtained in the detector 124 includes the following information.

[Expression 21]

$$\begin{cases} \Delta z_{21} & \cdots E_{samp} \dfrac{E_{ref2}}{\sqrt{\alpha_2^2+\beta_2^2}} \gamma(a_2\alpha_2 + c_2\beta_2 e^{-i\phi_2})J_{12} \equiv c3 \cdot J_{12} \\ \Delta z_{22} + 2\delta & \cdots E_{samp} \dfrac{E_{ref2}}{\sqrt{\alpha_2^2+\beta_2^2}} (b_2\alpha_2 + d_2\beta_2 e^{-i\phi_2})J_{21} \equiv c4 \cdot J_{21} \end{cases}$$

Equation 16

Here, c1 to c4 are complex constants. Therefore, if c1 to c4 are obtained in advance through measurement of a known wavelength plate, Equation 2 regarding the measurement Jones matrix can be obtained. However, it is necessary to position the two light beams with each other in terms of a phase level by performing a B scan.

What is claimed is:

1. An optical coherence tomography apparatus comprising:
    an OCT light source configured to emit a light;
    a first light splitter configured to split an optical path of light emitted from the OCT light source into a first measurement optical path by which measurement light is guided and a reference optical path by which a reference light is guided;
    a light guide optical system including a second light splitter through which the measurement light from the first measurement optical path is guided, the light guide optical system being configured to guide the measurement light to a test substance through the second light splitter, the second light splitter being configured to split light reflected from the test substance based on the measurement light, into the first measurement optical path and a second measurement optical path;
    a detection optical system configured to detect first interference between the reflected light having passed through the first measurement optical path and the reference light, and second interference between the reflected light having passed through the second measurement optical path and the reference light; and
    a calculation controller configured to process an output signal which is output from the detection optical system to obtain OCT data regarding the test substance.

2. The optical coherence tomography apparatus according to claim 1, wherein the second light splitter is configured to split the measurement light from the first measurement optical path into first measurement light and second measurement light.

3. The optical coherence tomography apparatus according to claim 2, wherein the light guide optical system includes a scanning optical system configured to scan the test substance to irradiate different positions on the test substance with the first measurement light and the second measurement light.

4. The optical coherence tomography apparatus according to claim 3, wherein the scanning optical system performs scanning with the first measurement light and the second measurement light in directions in which the first measurement light and the second measurement light are separated from each other.

5. The optical coherence tomography apparatus according to claim 1, wherein the calculation controller processes the output signal from the detection optical system to acquire at least two OCT tomographic images whose acquisition times are different from each other at the same part of the test substance and to acquire OCT motion contrast data regarding the same part of the set substance.

6. The optical coherence tomography apparatus according to claim 2, wherein the light guide optical system includes an optical path length difference generator configured to generate an optical path length difference between the first measurement light and the second measurement light.

7. The optical coherence tomography apparatus according to claim 1, further comprising a polarized light generator configured to generate at least two polarized measurement lights whose polarization components are different from each other based on the measurement light from the first measurement optical path.

8. The optical coherence tomography apparatus according to claim 7, wherein
the detection optical system detects interference between polarized reflected light which is reflected from the test substance based on the at least two measurement lights generated by the polarized light generator, and reference light,
the detection optical system detects first interference which is interference between the polarized reflected light having passed through the first measurement optical path and the reference light having passed through the reference optical path, and second interference which is interference between the polarized reflected light having passed through the second measurement optical path and reference light having passed through the reference optical path, and
the calculation controller processes the output signal from the detection optical system so as to analyze polarization characteristics of the test substance.

9. The optical coherence tomography apparatus according to claim 1,
wherein the calculation controller processes the output signal from the detection optical system to acquire a plurality of OCT data items and to obtain a combined image based on the plurality of OCT data items.

10. The optical coherence tomography apparatus according to claim 9, wherein the calculation controller obtains a motion contrast image as the combined image.

11. The optical coherence tomography apparatus according to claim 1, wherein the calculation controller processes the output signal from the detection optical system to acquire OCT data based on the first interference and acquire OCT data based on the second interference.

12. The optical coherence tomography apparatus according to claim 1,
wherein the detection optical system includes:
a first light detector configured to detect the first interference; and
a second light detector configured to detect the second interference.

13. The optical coherence tomography apparatus according to claim 1, wherein
at least one of the measurement optical path, the reference optical path, and the detection optical system is formed of a fiber optical system, and
the calculation controller performs calibration on a polarization component caused by the fiber optical system by using a measurement result in a known calibration sample to analyze polarization characteristics of the test substance.

* * * * *